United States Patent [19]
Spencer

[11] Patent Number: 5,871,612
[45] Date of Patent: Feb. 16, 1999

[54] WAFER FOR USE IN SELECTIVE CONNECTING AND DISCONNECTING OF PLASTIC TUBES

[75] Inventor: Dudley W.C. Spencer, Wilmington, Del.

[73] Assignee: Denco, Inc., Wilmington, Del.

[21] Appl. No.: 896,287

[22] Filed: Jul. 10, 1997

[51] Int. Cl.⁶ ..................................................... B32B 31/00
[52] U.S. Cl. .................... 156/503; 156/158; 156/304.2; 156/304.6; 156/499
[58] Field of Search ................................ 156/158, 304.1, 156/304.2, 304.5, 304.6, 499, 502, 503

[56] References Cited

U.S. PATENT DOCUMENTS

| | | | |
|---|---|---|---|
| 4,279,685 | 7/1981 | Barnett et al. | 156/509 |
| 5,141,592 | 8/1992 | Shaposka et al. | 156/515 |
| 5,156,701 | 10/1992 | Spencer et al. | 156/158 |
| 5,158,630 | 10/1992 | Shaposka et al. | 156/158 |
| 5,209,800 | 5/1993 | Spencer et al. | 156/158 |
| 5,279,685 | 1/1994 | Ivansons et al. | 156/158 |
| 5,397,425 | 3/1995 | Ivansons et al. | 156/503 |
| 5,525,186 | 6/1996 | Ivansons et al. | 156/503 |
| 5,632,852 | 5/1997 | Ivansons et al. | 156/503 |

*Primary Examiner*—James Sells
*Attorney, Agent, or Firm*—Connolly & Hutz

[57] ABSTRACT

A wafer for use in the selective connecting and disconnecting of plastic tubes incorporates a fuse in an aperture. The fuse is made of a laminate having light transmission characteristics which change after the wafer and its laminate have been heated. The wafer would be used in a device for connecting/disconnecting plastic tubes wherein the device includes a sensor which would deactivate the device if the sensor detects the change in light transmission characteristics thereby indicating that the wafer had been previously used.

8 Claims, 3 Drawing Sheets

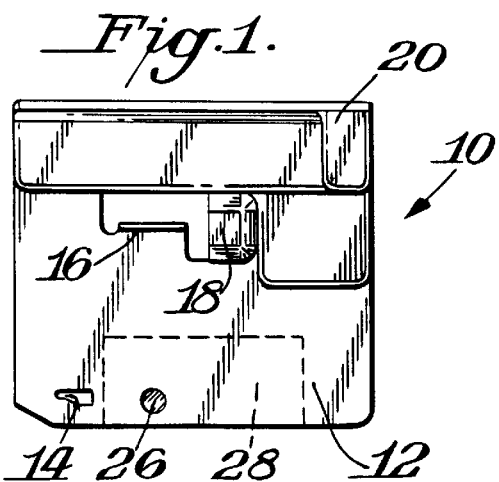
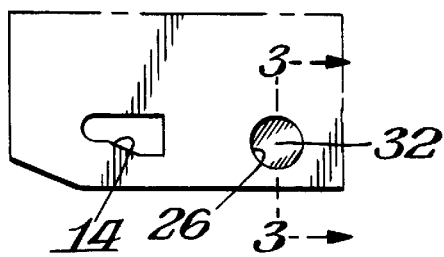
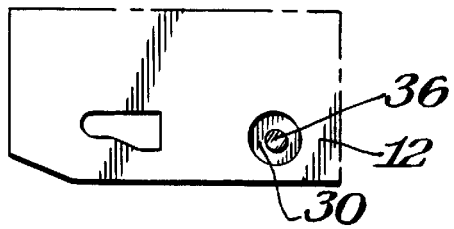
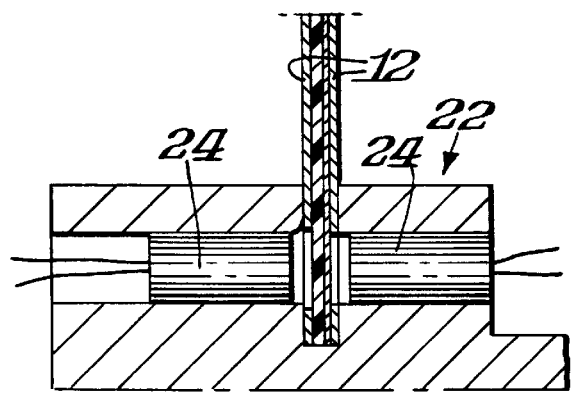
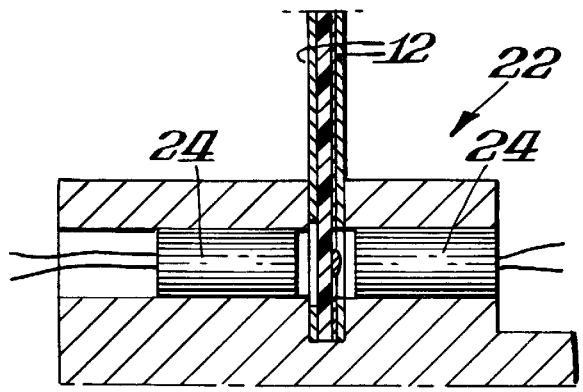

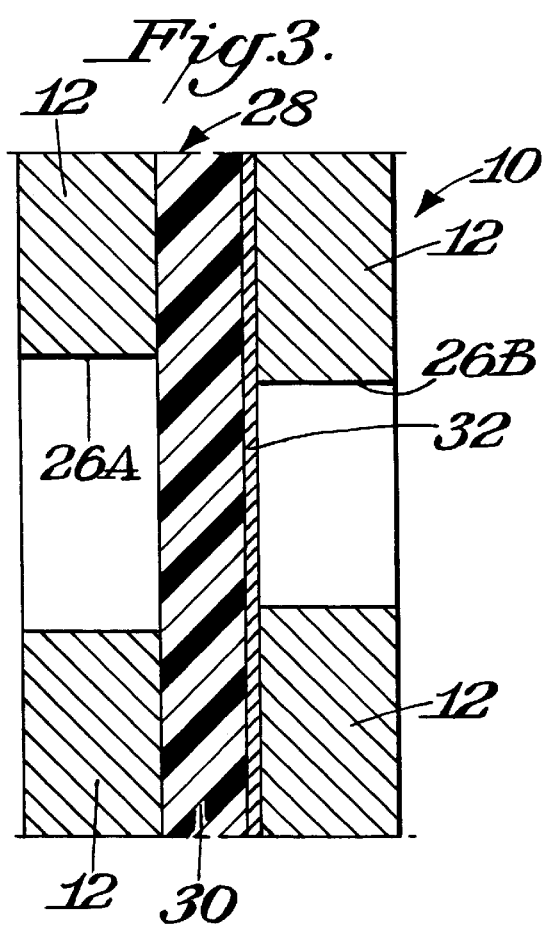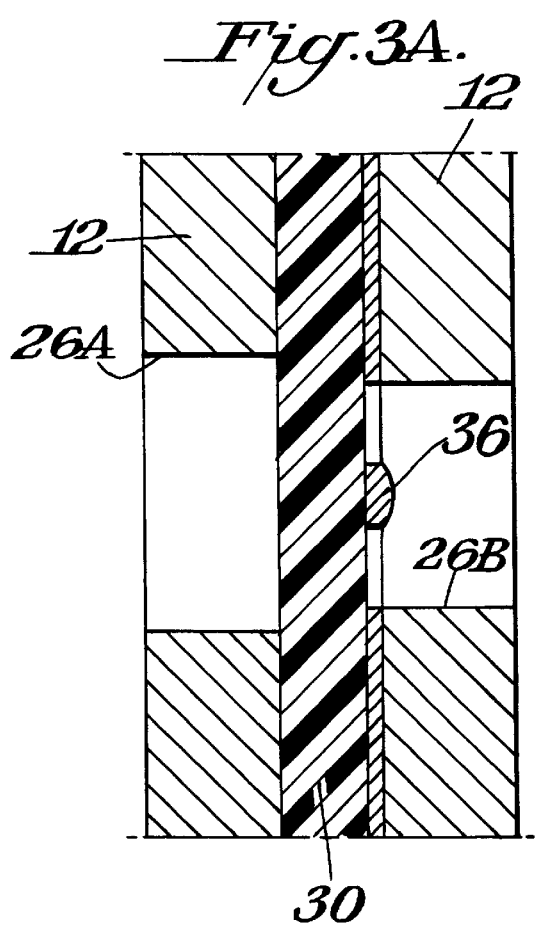

WAFER FOR USE IN SELECTIVE CONNECTING AND DISCONNECTING OF PLASTIC TUBES

BACKGROUND OF THE INVENTION

The present invention relates to wafers used for the selective connecting and disconnecting of plastic tubes such as would be used in total containment welding devices which have been described in various patents. The wafer is used in such systems as the component for heating the plastic tubes either as part of a process which disconnects a single tube into two tube sections for later welding of at least one tube section to the tube section of a different tube. When used for the connect process the wafer applies heat to separate tube ends causing the tube ends to melt so that the melted ends could be pressed together and form a unitary tube.

Frequently, the selective connecting and disconnecting of plastic tubes is performed in connection with medical techniques. Under certain circumstances it is necessary that the wafer be a single use wafer. The United States Food and Drug Administration, for example, has requirements prohibiting multiple use of devices such as wafers under certain conditions.

U.S. Pat. No. 5,525,186 discloses a particularly advantageous manner of assuring that a wafer would be used only once. As described in the '186 patent the wafer is provided with an aperture into which a sensing material is located. During the connect/disconnect operation the wafer moves past a sensor. When the sensor detects the presence of the sensing material in the aperture the process continues. If, however, no material is in the aperture, the absence of the material is sensed and the process is halted by deactivating the device. The particular sensing material disclosed in the '186 patent is a material which melts upon being heated. Thus, when a wafer is used for the first time the sensing material is initially in the aperture and detected by the sensor. Subsequently, when the wafer is heated the sensing material melts and there is no longer any material in the aperture. If an attempt is made to reuse the same wafer the sensor would detect the absence of the material or the open hole or aperture.

SUMMARY OF THE INVENTION

An object of this invention is to provide a wafer of the type disclosed in U.S. Pat. No. 5,525,186 wherein variations are utilized in connection with the material being sensed to assure single use.

In accordance with this invention a sensing material is provided in the aperture of the wafer having one set of light transmission characteristics prior to heating and different light transmission characteristics after the wafer is heated. Thus, a sensor would sense the proper light transmission characteristics for a wafer which has not yet been heated and would also sense the different light transmission characteristics which result after the wafer has been heated.

A main difference of the present invention from the arrangement in the '186 patent is that in the '186 patent after the wafer is heated the material melts and the aperture becomes completely open. With the present invention, however, after the wafer is heated material still remains in the aperture but has different light transmission characteristics than it had before heating.

THE DRAWINGS

FIG. 1 is a side elevational view of a wafer in accordance with this invention;

FIG. 2 is a side elevational view of a portion of the wafer shown in FIG. 1;

FIG. 3 is a cross-sectional view taken through FIG. 2 along the line 3—3;

FIG. 3A is a view similar to FIG. 3 showing the wafer after heating;

FIG. 4 is a fragmental cross-sectional end elevational view showing the wafer at the sensing station;

FIG. 5 is a fragmental side elevational view similar to FIG. 2 of the wafer after heating;

FIG. 6 is a view similar to FIG. 4 showing a wafer at the sensing station wherein the wafer had previously been heated.

DETAILED DESCRIPTION

Figure 7:
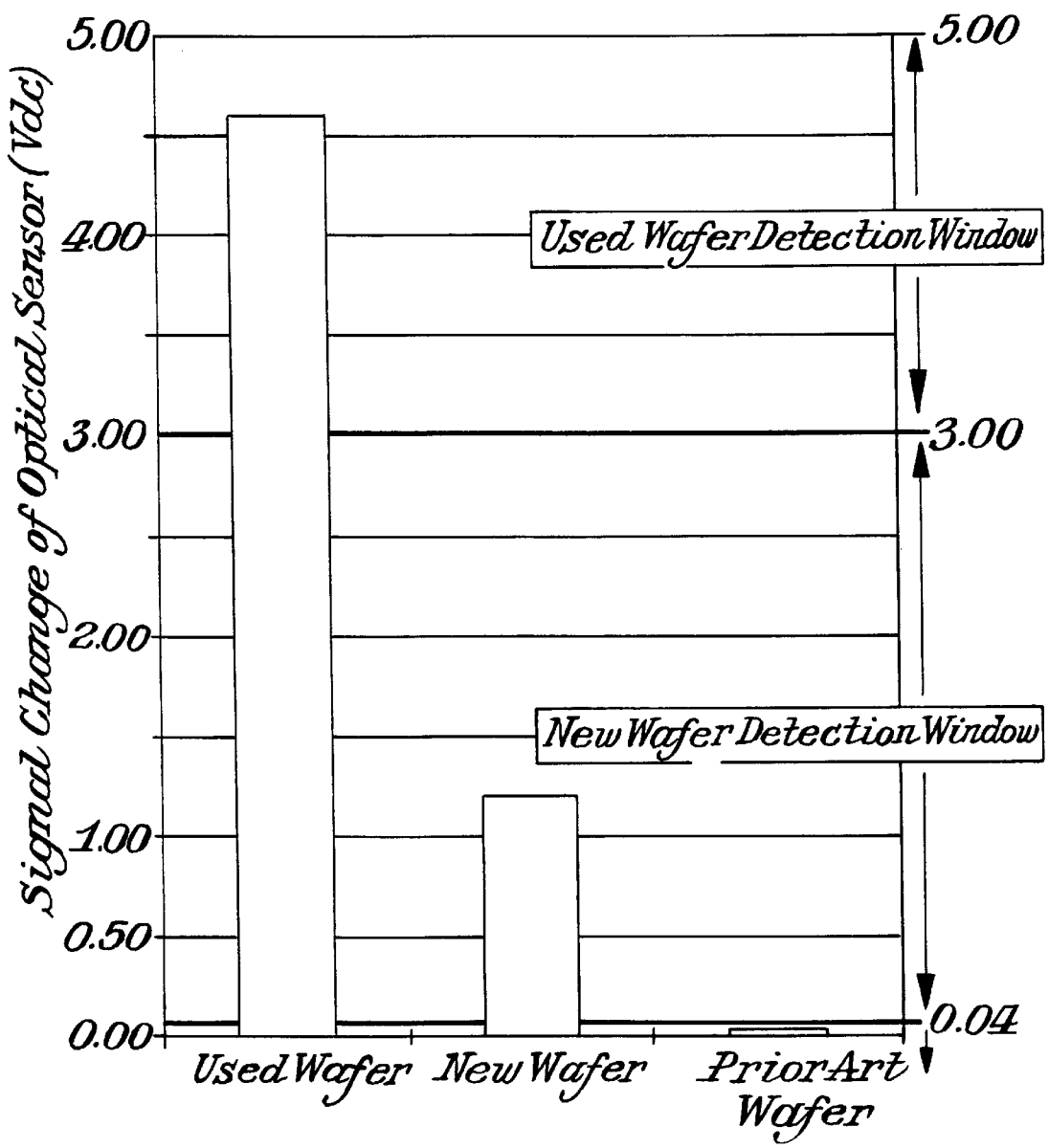
FIG. 7 is a bar chart comparing a new wafer in accordance with this invention and a used wafer in accordance with this invention and a wafer of conventional construction.

The present invention is based upon variations in wafer structure of the wafer shown in U.S. Pat. No. 5,525,186 the details of which are incorporated herein by reference thereto. In general, the invention involves the use of sensing material which acts as a fuse to either permit or prevent operation of the device using the wafer as part of a connecting/disconnecting of plastic tubes.

As shown in FIG. 1 wafer 10 is in the form of a flat plate having a pair of opposite sides 12,12 made of a heat conductive material such as copper. Wafer 10 also includes a cut-out or notch 14 for engagement by a pawl in the home position of the wafer in the manner described in U.S. Pat. No. 5,279,685, the details of which are incorporated herein by reference thereto. Wafer 10 also includes a wing 16 on each of its sides 12 and a scoop 18 on each of its sides generally in line with wing 26. The wings and scoops are located on the wafer at a position which would contact the melted tubes.

As also shown in FIG. 1 wafer 10 is mounted in a holder 20 the purpose of which is to mount the wafer in a carriage during the initial movement of the wafer, as described in U.S. Pat. No. 5,279,685. In operation, the wafer 10 mounted in holder 20 is moved downstream. The wafer is later detached from the holder. After performing its heating operation the wafer is removed from the device. During its movement wafer 10 passes through a sensing station 22 which is shown in FIGS. 4 and 6. Sensing station 22 includes a sensor 24 mounted in that path of movement of aperture 26 of wafer 10. Sensor 14 would sense the amount of light or light transmission through the wafer and more particularly through aperture 26. Such sensing could be in terms, for example, of a voltage reading which would differ from the voltage reading of the main wafer material 12 and would differ from the voltage reading of a completely open hole or aperture 26. If the sensor 14 does not detect the proper voltage which is representative of the proper amount of light being transmitted through aperture 26, then the device would be inactivated. This would mean that either the wafer 10 had been previously used and no longer has sensing material of proper light transmission characteristics or that there is a manufacturing defect and the sensing material was not mounted over the aperture 26.

As shown in FIG. 3 the sensing material comprises a laminate or composite 28 from a clear base material 30 such as mylar having a coating 32 of a material having limited light transmission characteristics, such as aluminum. Aperture 26 comprises a hole 26A in one wall of the copper wafer material 12 and a second hole 26B in the opposite wall. Holes 26A and 26B are concentric with each other. Hole 26A which is juxtaposed base layer 30 and is remote from second layer or coating 32 is larger than hole 26B. When the wafer 10 is disposed at the sensing station 22 shown in FIG. 4 light passes through hole 26B and then through laminate 28 and finally through hole 26A. Because of the light transmission properties of the aluminum layer 32, however, the signal resulting from the limited amount of light is of a value shown in FIG. 7 for the bar labeled new wafer. As long as the signal is within a certain range such as between 0.04 and 3.00 Vdc the device will continue to operate. The mylar 30 used in the laminate is a film oriented in two directions. Upon heating the film tends to shrink. The aluminum layer also shrinks but at a rate whereby it breaks into a glob or small circle indicated by the reference numeral 36 in FIG. 3A. The small circle is surrounded by a ring of clear mylar as shown in FIGS. 3A and 5. This results in the composite 28 having greater light transmission characteristics after heating than when the composite is in the initial condition shown in FIG. 3. Thus, after the wafer has been heated and the aluminum blob 36 is created, as shown in FIG. 3A, the light passes more readily through the composite through the clear ring around blob 36. By having the hole 26A oversized there is assurance of minimal interference of the light passing through wafer, as later described.

FIG. 6 shows the wafer 10 in the sensing station 22 if an attempt were made to reuse the laminate after it had already been heated. Because of the open ring around the blob 36 the signal is much higher as indicated by the bar graph of FIG. 7 for the bar labeled used wafer. As shown therein the signal is in excess of the 3.00 Vdc maximum. Under these conditions the device would be inactivated. FIG. 7 also illustrates the minimal signal that would be given if a conventional prior art wafer having no aperture were placed in the sensing station 22. Such signal would be less than the minimal acceptable stage to permit operation of the device.

The wafer 10 thus acts as a fuse to prevent operation of the device when a defective wafer is inserted in the device, namely a wafer which had previously used. Operation can only occur with a new or unused wafer having the sensing material 28 in its original pre-heated condition. Accordingly, the invention would function to identify three wafer conditions.

1. Solid Wafer

Defines as a wafer that completely blocks light transmission (Conventional prior art wafer without fuse, or a wafer with a masked fuse hole.)

2. New Wafer with Fuse

Fuse material must allow some light transmission. This will permit the sensor to detect fused wafers.

3. Used Wafer

A wafer with material that melts away to allow light to pass through the fuse hole.

The wafer detection system should be 100% reliable. This requires that all of the above conditions be met 100% of the time. Therefore there must be control over all of the parameters that affect the detection of used wafers.

The fused wafer should also be economical to produce, which means that the tolerance requirements of the fuse material and mounting holes falls within manufacturer capabilities.

The present system works with 5 mil mylar 30 that is coated on one side with aluminum 32 that permits 0.8% of the LED light to be transmitted through. When the wafer 10 is heated to 300 deg. C., the mylar 30 partially melts and shrinks. The aluminum coating 32 shrinks with the mylar and becomes a dense blob 36 in the middle of the fuse leaving a clear ring of PET around the blob of aluminum 36. This allows light to pass around the aluminum enabling the detection circuit to read the wafer as "used".

Parameters that affect used wafer detection are the following:

(Large Hole/Small Hole) vs. (Coated mylar fuse relationship)

1. The Large hole in the wafer determines the diameter of the initial mylar disk.

2. The diameter and thickness of the mylar disk determines the amount of shrinkage during the heating cycle.

3. The amount of shrinkage of the mylar determines the size of the aluminum blob.

4. The diameter of the aluminum blob determines the size of the small hole.

Note: The difference between the small hole 26B and large hole 26A must be big enough to create a step large enough as to not let any light bleed around the mylar fuse.

The composite 28 may take any suitable form and may be mounted in the aperture 26 in any suitable manner within the practice of this invention. As illustrated by the phantom lines in FIG. 1 the composite would be of sufficient size that it completely covers the aperture 26 without requiring undue manufacturing tolerances as would be required if a smaller size composite film were used. The strip or film 28 could be inserted between the two layers 12 of copper material used for the wafer and secured therein in any suitable manner, such as being secured within the one layer 12 having the oversize hole 26A.

The optical wafer sensor 14 that is in the carriage is also used for sensing the condition of the fuse. The device moves the carriage beyond the fuse hole location and gets a reference reading of the solid wafer. If a wafer is present the sensor scans forward past the fuse hole and records the maximum change in signal strength of the light passing through the fuse hole location. The following table represents the exiting optical sensing scale and limits.

delta 5.00 Vdc=100% Transparent (0% Blocked) Optical Density: 0.0000 Used Wafer delta 3.00 Vdc=60% Transparent (40% Blocked) Optical Density: 0.2219 New Wafer delta 0.04 Vdc=0.8% Transparent (99.2% Blocked) Optical Density: 1.398 Solid Wafer delta 0.00 Vdc=0% Transparent (100% Blocked) Optical Density infinite This scale gives a fairly large optical window for the mylar layer. Any coating or layer that blocks more than 40% but less than 99.2% of light would be detected as a new fuse.

Looking at the other end of the scale, physically it takes a narrow gap to drive the sensor into saturation indicating a used wafer. Therefore as long as the fuse shrinks consistently, exposing a narrow gap, used wafers will be detected. However, this condition creates some strict mounting requirements for the mylar fuse.

To ensure that no light bypasses the fuse once it is staked into the wafer the following measures would be taken.

The aluminum coating side 32 of the mylar 30 should face the small hole 26B. The light emitting side of the optical sensor is on the small hole side of the wafer. The non-coated side of the mylar will act like an optical pipe which will reflect the light towards the edges of the fuse.

The fuse should be staked in a way that assures that the fuse will not buckle and allow light to pass by.

The alignment of the small hole 26B vs. the large hole 26A should be controlled to prevent light bypassing the fuse.

Selection of the best combination of sizes of holes 26A and 26B and of thicknesses of mylar and aluminum can be determined in accordance with the range of signal which would be acceptable to permit operation of the device by the sensor indicating an unused wafer being in the sensing station.

What is claimed is:

1. A wafer for use in a device for selectively connecting and disconnecting plastic tubes, said wafer being in the form of a heatable flat plate having opposite sides, an aperture extending completely through said sides, a fuse located in said aperture, said fuse being made of a laminate material which covers said aperture prior to a heating of said wafer and remains covering said aperture subsequent to a heating of said wafer, said fuse having its light transmission properties increased after a heating of said wafer.

2. The wafer of claim 1 wherein said laminate comprises a base layer having a first light transmission properties, a second layer on said first layer, said second layer having second light transmission properties, said second layer shrinking upon being heated to create an open area in said second layer which permits light to pass directly through said base layer without passing through said second layer whereby the resulting light transmission properties of said laminate is increased after said laminate has been heated.

3. The wafer of claim 2 wherein said base layer is made of a transparent material.

4. The wafer of claim 3 wherein said aperture is formed by a first hole on one side of said laminate juxtaposed to said base layer and an aligned second hole formed on an opposite side of said laminate juxtaposed said second layer, and said first hole being of larger size than said second hole.

5. The wafer of claim 4 wherein said second layer shrinks to form a blob on said base layer with a clear ring of said base layer exposed around said blob.

6. The wafer of claim 5 wherein said base layer is made of mylar and said second layer is made of aluminum.

7. The wafer of claim 5 wherein said fuse blocks more than 40% and less than 99.2% of light passing through said fuse prior to heating.

8. The wafer of claim 5 wherein said fuse prior to heating permits a signal by an optical sensor in the range of 0.04 to 3.00 Vdc.

* * * * *